(12) United States Patent
White et al.

(10) Patent No.: US 9,889,071 B2
(45) Date of Patent: Feb. 13, 2018

(54) CALCIUM SULFATE-RESIN HYBRID MATERIALS AND METHODS OF USING AND MAKING THE SAME

(71) Applicant: THE REGENTS OF THE UNIVERSITY OF CALIFORNIA, Oakland, CA (US)

(72) Inventors: Shane White, Los Angeles, CA (US); Adam Inaba, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/777,469

(22) PCT Filed: Mar. 14, 2014

(86) PCT No.: PCT/US2014/029483
§ 371 (c)(1),
(2) Date: Sep. 15, 2015

(87) PCT Pub. No.: WO2014/144888
PCT Pub. Date: Sep. 18, 2014

(65) Prior Publication Data
US 2016/0045403 A1   Feb. 18, 2016

Related U.S. Application Data

(60) Provisional application No. 61/794,669, filed on Mar. 15, 2013.

(51) Int. Cl.
| | |
|---|---|
| A61K 6/083 | (2006.01) |
| A61C 5/04 | (2006.01) |
| A61L 27/44 | (2006.01) |
| C08K 3/30 | (2006.01) |
| C08K 3/36 | (2006.01) |
| A61K 33/06 | (2006.01) |
| A61L 27/50 | (2006.01) |
| A61C 5/50 | (2017.01) |

(52) U.S. Cl.
CPC .............. *A61K 6/0835* (2013.01); *A61C 5/50* (2017.02); *A61K 33/06* (2013.01); *A61L 27/446* (2013.01); *A61L 27/50* (2013.01); *C08K 3/30* (2013.01); *C08K 3/36* (2013.01); *A61L 2430/02* (2013.01); *C08K 2003/3045* (2013.01)

(58) Field of Classification Search
None
See application file for complete search history.

(56) References Cited

U.S. PATENT DOCUMENTS

| | | | | |
|---|---|---|---|---|
| 3,919,773 | A * | 11/1975 | Freeman | A61K 6/083 433/175 |
| 6,821,462 | B2 * | 11/2004 | Schulman | A61C 13/0003 164/34 |
| 7,700,667 | B2 * | 4/2010 | Jia | A61K 6/0023 106/35 |
| 2002/0022677 | A1 | 2/2002 | Teramae et al. | |
| 2004/0002037 | A1 * | 1/2004 | Orlowski | A61K 6/0023 433/220 |
| 2005/0020720 | A1 * | 1/2005 | Dickens | A61K 6/0017 523/115 |
| 2005/0192374 | A1 * | 9/2005 | Jia | A61K 6/0023 523/116 |
| 2007/0233258 | A1 * | 10/2007 | Hestad | A61B 17/7098 623/17.12 |
| 2008/0145820 | A1 * | 6/2008 | Karmaker | A61C 13/0003 433/220 |
| 2010/0331978 | A1 * | 12/2010 | Stromme | A61L 24/001 623/11.11 |
| 2011/0097420 | A1 | 4/2011 | Lin et al. | |
| 2011/0104644 | A1 | 5/2011 | Primus et al. | |
| 2011/0206975 | A1 * | 8/2011 | Ichinose | H01M 2/0207 429/152 |
| 2011/0244431 | A1 | 10/2011 | Shinozaki et al. | |
| 2012/0270184 | A1 | 10/2012 | Richard et al. | |

OTHER PUBLICATIONS

PCT International Search Report and Written Opinion from PCT/US2014/029483 dated Aug. 24, 2014.

* cited by examiner

*Primary Examiner* — Joseph D Anthony
(74) *Attorney, Agent, or Firm* — Gates & Cooper, LLP

(57) ABSTRACT

The present invention discloses a new family of calcium sulfate resin-modified hybrid (CSRH) materials and methods of making and using the same.

6 Claims, No Drawings

CALCIUM SULFATE-RESIN HYBRID MATERIALS AND METHODS OF USING AND MAKING THE SAME

CROSS-REFERENCE TO RELATED APPLICATIONS

The application is a U.S. national stage entry of International Application No. PCT/US2014/029483, which in turn claims priority to U.S. provisional application No. 61/794,669 filed on Mar. 15, 2013 and also entitled "CALCIUM SULFATE-RESIN HYBRID MATERIALS AND METHODS OF USING AND MAKING THE SAME," which is hereby incorporated by reference herein in its entirety.

FIELD OF THE INVENTION

The present invention relates generally to biomedical materials.

BACKGROUND OF THE INVENTION

An ideal material for root end-filling, perforation repair, treating resorptive defects, treating vital exposed pulps, and obturating immature non-vital teeth has long been sought. Silver amalgam was one of the first materials used as a root end filling material. But it can be cytotoxic, stain the soft tissues, corrodes, and does not provide an effective apical seal (1-3). Therefore, alternative endodontic materials such as Super EBA, glass-ionomer, resin-composite, and resin-modified glass-ionomers (RMGI) have all been used. Although some of these materials have some desirable properties, they are also insufficient in other aspects. For example, Super EBA has relatively poor biocompatibility and poor physical properties (4). Resin composites and some resin-modified glass-ionomers have a desirable attribute, that is, being light curable, however such resin-composites and glass-ionomer materials are intolerant of moisture. Resin-modified glass-ionomers are less user-sensitive and more tolerant of moisture, but still require a dry field (5). Therefore, the search for the ideal endodontic root-end filling and repair material continues. Recommended properties of an ideal endodontic root-end filling and repair material include: dimensional stability, good sealing ability, insolubility, tolerance to moisture, easy manipulation, a short and controllable set time, biocompatible, and the ability to promote regeneration of a normal periodontium.

MTA (mineral trioxide aggregate) was introduced in 1993; it is the most well documented, well accepted and widely used material (6-16). MTA is biocompatible, allows for regeneration of the attachment apparatus and regeneration of bone (17, 18). MTA is dimensionally stable and provides a superior apical seal compared to other materials (19). MTA is both biocompatible and bacteriostatic, likely due to a basic pH. However, MTA has somewhat demanding handling properties, a very long setting time, poor abrasion resistance, only fair resistance to dissolution, and acceptable, but not excellent physical properties (12-14). Indeed, the manufacturer of MTA requires that the set of MTA has to be checked at a minimum of 4 hours after placement, and it is recommended that MTA should not be placed in clinical situations where it might become exposed to the oral environment. MTA and materials closely related thereto are covered by a range, or ladder, of patents that extend well into the future. Currently, MTA is approximately an order of magnitude more expensive than its alternatives; and this limits its more widespread usage.

Therefore, there remains a need for alternative endodontic filling materials.

Therefore, it is an objective of the present invention to provide an alternative endodontic filling material.

The embodiments below address the above needs and objectives.

SUMMARY OF THE INVENTION

Provided herein is a new calcium sulfate-resin hybrid (CSRH) material for use as an endodontic root-end filling, repair, obturating and pulp capping material. The CSRH can be used as a biomedical material such as an endodontic filling material that will have the advantages of both MTA (mineral trioxide aggregate) and of resin-modified glass-ionomers (i.e. performing well in a moist environment, being bacteriostatic, biocompatible, being easy to manipulate, having a command set, not needing its set to be checked), but have superior physical properties (i.e. resistance to abrasion and dissolution), wider clinical applications, and a low cost In one aspect of the present invention, it is disclosed a calcium sulfate-resin hybrid (CSRH) material composition, comprising a powder component and a liquid component, wherein the powder component comprises calcium sulfate, wherein the liquid component comprises bisGMA (bisphenol-a-glycidyl methacrylate), photoinitiator, and photoinitiators, and wherein the composition is a fast setting composition.

In some embodiments of the invention composition, the powder component further comprises a silicate filler and a radioopacifier, and the liquid further optionally comprises HEMA (ydroxyethyl methacrylate), TEGDMA (triethylene glycol dimethacrylate), and/or polyacrylic acid and polyacrylic acid where each of HEMA, TEGMA, polyacrylic acid or combination thereof is optional.

In some embodiments of the invention composition, the liquid component further comprises water.

In some embodiments of the invention composition, optionally in combination with any or all of the above various embodiments, the composition reaches an initial set immediately upon light curing after application to a subject, and having a wet Vickers microhardness of about 1 GPa or higher.

In some embodiments of the invention composition, optionally in combination with any or all of the above various embodiments, the calcium sulfate comprises from 30-66% by weight of the composition.

In some embodiments of the invention composition, optionally in combination with any or all of the above various embodiments, the bisGMA, photoinitiator, and silicate filler together comprise 10-30% by weight of the composition.

In some embodiments of the invention composition, optionally in combination with any or all of the above various embodiments, the TEGDMA comprises 0-30% by weight of the composition.

In some embodiments of the invention composition, optionally in combination with any or all of the above various embodiments, the polyacrylic acid comprises 0-40% by weight of the composition.

In some embodiments of the invention composition, optionally in combination with any or all of the above various embodiments, the water comprises 6-15% by weight of the composition.

In some embodiments of the invention composition, optionally in combination with any or all of the above various embodiments, the radio-opacifier comprises 4-10% by weight of the composition.

In some embodiments of the invention composition, optionally in combination with any or all of the above various embodiments, HEMA comprises 0-15% by weight of the composition.

In some embodiments of the invention composition, optionally in combination with any or all of the above various embodiments, the radio-opacifier is barium sulfate.

In another aspect of the present invention, it is provided a method of fabricating a medical device, comprising:
providing a composition comprising a powder component and a liquid component, and
forming a semi-solid formulation of the composition,
wherein the powder component comprises calcium sulfate,
wherein the liquid component comprises bisGMA (bisphenol-a-glycidyl methacrylate) and photoinitiators, and
wherein the composition is a fast setting composition.

In some embodiments of the invention method, the powder component further comprises a silicate filler and a radioopacifier, and the liquid further optionally comprises HEMA (ydroxyethyl methacrylate), TEGDMA (triethylene glycol dimethacrylate), and/or polyacrylic acid and polyacrylic acid where each of HEMA, TEGMA, polyacrylic acid or combination thereof is optional.

In some embodiments of the invention method, optionally in combination with any or all of the above various embodiments, the liquid component further comprises water.

In some embodiments of the invention method, optionally in combination with any or all of the above various embodiments, the composition reaches an initial set immediately upon light curing after application to a subject, and having a wet Vickers microhardness of about 1 GPa or higher.

In some embodiments of the invention method, optionally in combination with any or all of the above various embodiments, the calcium sulfate comprises from 30-66% by weight of the composition.

In some embodiments of the invention method, optionally in combination with any or all of the above various embodiments, the bisGMA, photoinitiator, and silicate filler together comprise 10-30% by weight of the composition.

In some embodiments of the invention method, optionally in combination with any or all of the above various embodiments, the TEGDMA comprises 0-30% by weight of the composition.

In some embodiments of the invention method, optionally in combination with any or all of the above various embodiments, the polyacrylic acid comprises 0-40% by weight of the composition.

In some embodiments of the invention method, optionally in combination with any or all of the above various embodiments, the water comprises 6-15% by weight of the composition.

In some embodiments of the invention method, optionally in combination with any or all of the above various embodiments, the radio-opacifier comprises 4-10% by weight of the composition.

In some embodiments of the invention method, optionally in combination with any or all of the above various embodiments, HEMA comprises 0-15% by weight of the composition.

In some embodiments of the invention method, optionally in combination with any or all of the above various embodiments, the radio-opacifier is barium sulfate.

In a further aspect of the present invention, it is provided a method of treating or ameliorating a disorder, comprising:
applying to a subject a composition comprising a powder component and a liquid component, and
photo-setting the composition to cause it to reach an initial set immediately upon light curing after application to a subject and have a wet Vickers microhardness of about 0.1 GPa or higher;
wherein the powder component comprises calcium sulfate,
wherein the liquid component comprises bisGMA (bisphenol-a-glycidyl methacrylate) and photoinitiators, and
wherein the composition is a fast setting composition.

In some embodiments of the invention method, the powder component further comprises a silicate filler and a radioopacifier, and the liquid further optionally comprises HEMA (ydroxyethyl methacrylate), TEGDMA (triethylene glycol dimethacrylate), and/or polyacrylic acid and polyacrylic acid where each of HEMA, TEGMA, polyacrylic acid or combination thereof is optional.

In some embodiments of the invention method, optionally in combination with any or all of the above various embodiments, the liquid component further comprises water.

In some embodiments of the invention method, optionally in combination with any or all of the above various embodiments, the composition reaches an initial set immediately upon light curing after application to a subject, and having a wet Vickers microhardness of about 1 GPa or higher.

In some embodiments of the invention method, optionally in combination with any or all of the above various embodiments, the calcium sulfate comprises from 30-66% by weight of the composition.

In some embodiments of the invention method, optionally in combination with any or all of the above various embodiments, the bisGMA, photoinitiator, and silicate filler together comprise 10-30% by weight of the composition.

In some embodiments of the invention method, optionally in combination with any or all of the above various embodiments, the TEGDMA comprises 0-30% by weight of the composition.

In some embodiments of the invention method, optionally in combination with any or all of the above various embodiments, the polyacrylic acid comprises 0-40% by weight of the composition.

In some embodiments of the invention method, optionally in combination with any or all of the above various embodiments, the water comprises 6-15% by weight of the composition.

In some embodiments of the invention method, optionally in combination with any or all of the above various embodiments, the radio-opacifier comprises 4-10% by weight of the composition.

In some embodiments of the invention method, optionally in combination with any or all of the above various embodiments, HEMA comprises 0-15% by weight of the composition.

In some embodiments of the invention method, optionally in combination with any or all of the above various embodiments, the radio-opacifier is barium sulfate.

In some embodiments of the invention method, optionally in combination with any or all of the above various embodiments, the disorder is a pulpal disorder.

In some embodiments of the invention method, optionally in combination with any or all of the above various embodiments, the disorder is a bone defect or injury.

The subject can be an animal or a patient.

DETAILED DESCRIPTION OF THE INVENTION

We describe herein a new calcium sulfate-resin hybrid (CSRH) material for use as an endodontic root-end filling, repair, obturating and/or pulp capping material. The CSRH can be used as a biomedical material such as an endodontic filling material that will have the advantages of both MTA and of resin-modified glass-ionomers (i.e. performing well in a moist environment, being bacteriostatic, biocompatible, being easy to manipulate, having a command set, not needing its set to be checked), but have superior physical properties (i.e. resistance to abrasion and dissolution), wider clinical applications, and a low cost.

In one aspect of the present invention, it is disclosed a calcium sulfate-resin hybrid (CSRH) material composition, comprising a powder component and a liquid component, wherein the powder component comprises calcium sulfate, wherein the liquid component comprises bisGMA (bisphenol-a-glycidyl methacrylate), photoinitiator, and photoinitiators, and wherein the composition is a fast setting composition.

In some embodiments of the invention composition, the powder component further comprises a silicate filler and a radioopacifier, and the liquid further optionally comprises HEMA (ydroxyethyl methacrylate), TEGDMA (triethylene glycol dimethacrylate), and/or polyacrylic acid and polyacrylic acid where each of HEMA, TEGMA, polyacrylic acid or combination thereof is optional.

In some embodiments of the invention composition, the liquid component further comprises water.

The term "fast setting", as used herein, means that the composition has an initial set immediately upon light curing after application to a subject. In some embodiments, the term refers to the composition has an initial set immediately upon light curing after application to a subject and a wet Vickers microhardness of about 0.1 GPa or higher.

In some embodiments of the invention composition, optionally in combination with any or all of the above various embodiments, the composition reaches an initial set immediately upon light curing after application to a subject, and having a wet Vickers microhardness of about 0.1 GPa or higher.

In some embodiments of the invention composition, optionally in combination with any or all of the above various embodiments, the calcium sulfate comprises from 30-66% by weight of the composition.

In some embodiments of the invention composition, optionally in combination with any or all of the above various embodiments, the bisGMA, photoinitiator, and silicate filler together comprise 10-30% by weight of the composition.

In some embodiments of the invention composition, optionally in combination with any or all of the above various embodiments, the TEGDMA comprises 0-30% by weight of the composition.

In some embodiments of the invention composition, optionally in combination with any or all of the above various embodiments, the polyacrylic acid comprises 0-40% by weight of the composition.

In some embodiments of the invention composition, optionally in combination with any or all of the above various embodiments, the water comprises 6-15% by weight of the composition.

In some embodiments of the invention composition, optionally in combination with any or all of the above various embodiments, the radio-opacifier comprises 4-10% by weight of the composition.

In some embodiments of the invention composition, optionally in combination with any or all of the above various embodiments, HEMA comprises 0-15% by weight of the composition.

In some embodiments of the invention composition, optionally in combination with any or all of the above various embodiments, the radio-opacifier is barium sulfate.

Endodontic Materials

Conventional Glass-ionomer (GI) Materials

Conventional glass-ionomer (GI) materials have many desirable attributes and were introduced for use as endodontic sealers (e.g. Ketac Endo, 3M/ESPE). However, GIs are extremely sensitive to undue moisture during the first stage of their setting reaction—which takes approximately 10 minutes. Therefore, we previously investigated emergent RMGI materials (also known as compomers) and determined that they were less sensitive to moisture than a conventional glass-ionomer cement control (5). However, drier environments still produced superior specimens. We also measured bone infill following apical surgery and found almost complete infill using a RMGI material within 18 months (20). However, in total, our work indicated that they are not suitable for applications where a dry field cannot be maintained until the setting reaction is complete, so both GI and RMGI's endodontic applications are inherently limited.

Portland Cement Based Materials

Others have tried to improve Portland cement based materials, particularly their slow set, that needs to be checked at least 4 hours after placement—a great clinical inconvenience, practical disadvantage, and expense. Gandolfi et al (21) have created a light-curable calcium-silicate cement containing a HEMA-TEGDMA-based resin (lc-MTA). The poly-HEMA-TEGDMA hydrophilic resin creates the conditions (calcium release and functional groups able to chelate Ca ions) for a bioactive fast setting light-curable material. Their results showed that the lc-MTA had a rapid-setting time (2 minutes), low solubility, high calcium release and alkalinizing power (pH 10-12). Another study investigated the physical properties and cyototoxicity of a new root-end filling material (EPC) containing a mixture of epoxy resin and Portland cement as a MTA substitute. EPC was shown to be a useful material for root-end filling, with favorable radio-opacity, short setting time, low microleakage, and clinically acceptable low cytotoxicity (22). Neither of these materials have been brought to market, patent and licensing issues may slow their adoption. Epoxy resins are more stable in the presence of moisture than many other resins which lack durable covalent crosslinking, but this is only relative—resins with durable covalent cross linking, e.g. bisGMA and TEGDMA can be much more stable in damp environments—like dentin which is contains approximately 40% water by weight. Furthermore, the relatively poor solubility and abrasion resistance of Portland cement based materials likely cannot be overcome by the addition of polymers without degrading their setting reaction—a counterproductive effort.

Calcium Sulfate-resin Hybrid (CSRH) Materials.

Calcium sulfate has been used in the medicine and dentistry for almost 2 centuries because it is inexpensive, abundant, moisture tolerant, biocompatible, and can promote bone regeneration. However, calcium sulfate is relatively weak and soluble. Implantation studies have proven that calcium sulfate resorbs quickly and produces a minimal host inflammatory response. Studies evaluating the interactions between host cells and calcium sulfate have also provided promising results regarding calcium sulfate's biocompatibility (23, 24). Payne et at (25) have studied the ability of human fibroblast to migrate over commonly used GTR barriers in response to a chemotactic stimulus, showing that fibroblasts were able to migrate farther over calcium sulfate than other materials. Furthermore, SEM examination of the fibroblast in contact with calcium sulfate exhibited normal morphology, and fibroblasts in contact with other GTR barriers had abnormal morphology. This further indicates the ability of calcium sulfate to co-exist without damaging host cells. Importantly, the long use of calcium sulfate as a bone grafting material means that it is not patent protected for many endodontic applications Calcium sulfate has the ability to promote osteogenesis, but the mechanism remains unclear. Some authors believe that as calcium sulfate resorbs, it acts as a "guide" for bone mineralization. Resorption of calcium sulfate increases calcium ions concentrations in surrounding bone. With an increased concentration of extracellular calcium ions, the homeostasis theory of bone suggests that remodeling tips the balance towards bone formation (23, 24). Calcium ions may stimulate the calcium receptors on osteoblasts and result in osteoblast proliferation, differentiation, and osteoid synthesis (26). Conversely, calcium receptors on osteoclasts will also be stimulated and decrease their ability to resorb bone (27). Finally, others have proved that calcium sulfate plays an active role in osteogenesis. Walsh et at (28) used calcium sulfate pellets to fill in cancellous bone defects in femoral bones; showing that this increased concentrations of bone morphogenic protein (BMP)-2, BMP-7, transforming growth factor-b (TGF-b), and platelet-derived growth factor (PDGF), all of which play a role in connective tissue regeneration.

Calcium sulfate's use in endodontics has been limited to use as an effective hemostatic agent and bone graft material (29). Pecora et at (30) explains that calcium sulfate can be used as an adjunctive bone graft material for extensive periradicular lesions because it can promote osseous healing. Mittal et at and Taneja et at (31, 32) have shown that calcium sulfate is not an effective internal matrix for perforation repairs because its lack of sealing ability.

By incorporating hydrophilic resins, we disclose a calcium sulfate material that is still hydrophilic, moisture-tolerant, biocompatible, and osteoinductive; but is more stable, less soluble, and—of critical importance—adhesive to dentin, has a light cure command-set capability—both of great importance during endodontic surgery—and has superior handling properties—important for clinical acceptance by dentists. This is somewhat analogous to the addition of resins to glass-ionomers to produce successful hybrid materials (5). It has many of the advantages of MTA, including an alkaline pH, but with superior physical properties, setting time, user friendliness, and potentially lower cost.

The CSRH disclosed herein is a family of materials containing calcium sulfate as well as: polyacrylic acid; HEMA; BisGMA; TEDGMA; established polymerization initiators; silicate filler, radio-opacifiers and water. All of these components have been well studied and widely used in prior dental and medical products, materials and devices. This assures a smooth pathway through future biocompatibility testing and FDA approval.

As used herein, the term MTA refers to mineral trioxide aggregate, which is commonly known and used in various dental applications.

As used herein, the term fast setting shall mean a setting time of the composition disclosed herein after photo-initiation of about less than one minute to immediately reach an initial set. An endotontic material is considered to have an initial set after it achieves a Vickers microhardness of about 0.1 GPa; for a full set, a Vickers microhardness of about 0.2 GPa is desired.

Other Materials

In some embodiments, the composition of invention can further include one or more biodurable or biodegradable polymers. Biodegradable polymers can be natural or synthetic polymers, examples of which include, e.g., poly (.alpha.-hydroxy acids) such as poly (L-lactide) (PLLA), poly (D, L-lactide) (PDLLA), polyglycolide (PGA), poly (lactide-co-glycolide (PLGA), poly (-caprolactone), poly (trimethylene carbonate), poly (p-dioxanone), poly (-caprolactone-co-glycolide), poly (glycolide-co-trimethylene carbonate) poly (D, L-lactide-co-trimethylene carbonate), polyarylates, polyhydroxybutyrate (PHB), polyanhydrides, poly (anhydride-co-imide), propylene-co-fumarates, polylactones, polyesters, polycarbonates, polyanionic polymers, polyanhydrides, polyester-amides, poly(amino-acids), homopolypeptides, poly(phosphazenes), poly (glaxanone), polysaccharides, and poly(orthoesters), polyglactin, polyglactic acid, polyaldonic acid, collagen, gelatin, hyaluronic acid, alginate polyalkanoates; copolymers and admixtures thereof, and any derivatives and modifications. See for example, U.S. Pat. No. 4,563,489, and PCT Int. Appl. #WO/03024316, herein incorporated by reference. Examples of biodurable polymers include, but are not limited to, poly(ethylene glycol), alkylcellulose (including hydroxyalkylcellulose), including methylcellulose, ethylcellulose, hydroxyethylcellulose, hydroxypropylcellulose, hydroxypropyl-methylcellulose, and carboxymethylcellulose, polyoxyethylene oxide, carboxyvinyl polymer, poly (vinylpyrrolidinone) (PVP), poly(vinyl alcohol), and poly (ethylene acetate).

Method of Making the Composition of Invention

In another aspect of the present invention, it is provided a method of fabricating a medical device, comprising
  providing a composition comprising a powder component and a liquid component, and
  forming a semi-solid formulation of the composition,
  wherein the powder component comprises calcium sulfate,
  wherein the liquid component comprises bisGMA (bisphenol-a-glycidyl methacrylate) and photoinitiators, and
  wherein the composition is a fast setting composition.

In some embodiments of the invention method, the powder component further comprises a silicate filler and a radioopacifier, and the liquid further optionally comprises HEMA (ydroxyethyl methacrylate), TEGDMA (triethylene glycol dimethacrylate), and/or polyacrylic acid and polyacrylic acid where each of HEMA, TEGMA, polyacrylic acid or combination thereof is optional.

In some embodiments of the invention method, optionally in combination with any or all of the above various embodiments, the liquid component further comprises water.

In some embodiments of the invention method, optionally in combination with any or all of the above various embodiments, the composition reaches an initial set immediately upon light curing after application to a subject, and having a wet Vickers microhardness of about 1 GPa or higher.

In some embodiments of the invention method, optionally in combination with any or all of the above various embodiments, the calcium sulfate comprises from 30-66% by weight of the composition.

In some embodiments of the invention method, optionally in combination with any or all of the above various embodiments, the bisGMA, photoinitiator, and silicate filler together comprise 10-30% by weight of the composition.

In some embodiments of the invention method, optionally in combination with any or all of the above various embodiments, the TEGDMA comprises 0-30% by weight of the composition.

In some embodiments of the invention method, optionally in combination with any or all of the above various embodiments, the polyacrylic acid comprises 0-40% by weight of the composition.

In some embodiments of the invention method, optionally in combination with any or all of the above various embodiments, the water comprises 6-15% by weight of the composition.

In some embodiments of the invention method, optionally in combination with any or all of the above various embodiments, the radio-opacifier comprises 4-10% by weight of the composition.

In some embodiments of the invention method, optionally in combination with any or all of the above various embodiments, HEMA comprises 0-15% by weight of the composition.

In some embodiments of the invention method, optionally in combination with any or all of the above various embodiments, the radio-opacifier is barium sulfate.

As an example of the method of fabricating the invention composition, CSRH materials are formed and evaluated. In general, the CSRH material can be evaluated against one or more controls. CSRH materials performing in an inferior manner to 2 or more their control comparators can be screened out. The remaining materials are then be subjected to biocompatibility testing, toxicity and immunology, and can be subjected to animal model testing and eventual clinical trials in due course of product development and regulatory review. Sample sizes are based upon prior work, but power analyses can be performed after preliminary data is gathered for each task so as to ensure adequacy.

In some embodiments, an exemplary method of making a composition of invention includes any one, any combination, or all the steps described below. These steps can be carried out in any order. Designation of a step as step (1), (2), or any number shall not mean the step has to be performed in that particular sequence.

(1) Creating a Family of Related but Differing CSRH Materials.

The CSRH mixture is composed of a powder and a liquid component. The powder component includes a fast-setting calcium sulfate, silicate fillers, and radio-opacifiers. The liquid component includes bisGMA, photoinitiators, HEMA, TEGDMA, polyacrylic acid, and water.

TABLE 1

| Range of wet liquid and dry inorganic components (% by weight) | |
|---|---|
| Calcium sulfate | 30-66% |
| BisGMA, photoinitiators, and silicate fillers | 10-30% |
| TEGDMA | 0-30% |
| Polyacrylic acid | 0-40% |
| Water | 6-15% |
| Radio-opacifiers, barium sulfate | 4-10% |
| HEMA | 0-15% |

BisGMA will allow co-polymerization with HEMA and polyacrylic acid, the use light curing photoinitiators and an overall resinous matrix to provide stability and resistance to dissolution and abrasion (37-39). TEGDMA is a diluent of bisGMA with excellent viscosity and copolymerization behaviors, it increases wettability of dentin, promoting adhesion (40). Silicate fillers will provide stability and barium sulfate (radio-opacificer) can be used to provide radiodensity (39). Polyacrylic acid is included in the mixture because it is a hydrophilic polymer, which may form an acid-base reaction with calcium sulfate, allow more water incorporation, and co-polymerize with bisGMA and HEMA (hydroxyethyl methacrylate), and provide additional adhesion to dentin (41, 42). Water-soluble polymers of polyacrylic acid have also been shown to increase induction time, decrease the rate of precipitation, and alter crysal morphology (43). HEMA is a polar highly hydrophilic resin, widely used in dentin bonding agents and contact lenses, which will allow water incorporation, adhesion to dentin, and co-polymerization/interaction with calcium sulfate (37,38). Sufficient water is necessary to allow the calcium sulfate setting reaction.

Other materials can be used to replace one or more or all of the components above, as long as such materials form a composition having properties, e.g., chemical properties, physical properties and biocompatibility properties that render them suitable as an endodontic filling material or orthopedic application. In some embodiments, the calcium sulfate can be replaced by calcium phosphate, for example, and bisGMA (bisphenol A-glycidyl methacrylate), TEGDMA (tetraethyleneglycol dimethacrylate), and/or HEMA can be replaced by other methacrylic acid or methacrylate monomers.

(2) Identifying the Amount of Barium Sulfate Necessary to Achieve Adequate Radiodensity.

Establish adequate radiodensity parameters for the initial CRSH material family. This can be compared to current commercial gutta percha to determine the minimum percentage of barium sulfate. An established aluminum step gage for measuring radiodensity and #30 gutta percha cones (Sybron, Orange, Calif.) can be used. It is expected that 20 specimens can be made and tested.

(3) Identifying CSRH Materials with Adequate Initial Set Using Microhardness Screening.

Basic Screening of Setting.

Vickers microhardness testing can be used to screen materials for adequacy of set. Specimens can be light-cured and embedded in epoxy resin small discoid molds, height and diameter 3 mm. The specimens can be stored in 100% humidity for 1 hour and then in water for 23 additional hours, surface finished, and subjected to Vickers microhardness testing as previously described (44). Each mixture will have 5 specimens, which will undergo 5 repetitions, i.e. 150 specimens and 750 tests. The criteria can be the hardness of established endodontic surgical control materials, MTA and Geristore.

(4) Identify CSRH Materials with Adequate Strength Using Mechanical Test Screening.

Compressive Strength and Proportional Limit, and Tensile Strength, Screenings.

Although mechanical properties are not paramount for endodontic applications, ideally such materials should have properties equivalent to those of the natural material being repaired or replaced, dentin. Teeth are flexible and deform when loaded; unequal deformation leads to stress concentrations, separation of the repair or replacement and gap formation. This is a likely area for considerable improvement over existing endodontic retrofilling, repair, and pulp capping materials. However, inadequate cross-linking, and or inorganic filler content of resinous cements can lead to very poor mechanical properties (44).

For compressive testing, cylindrical specimens, 6 mm high and 4 mm in diameter, can be made and stored at 37° C. in 100% humidity for 1 hour, before being transferred to water at 37° C. for an additional 23 hours. Wet specimens can be loaded in compression at crosshead rates of 0.5 mm/min with a servohydraulic universal testing machine with a 20,000-lb load frame (Instron, Canton, Mass.) and the load plotted against time, n=10 per material. The American Dental Association specifications for testing cements recommend a crosshead rate of 0.5 mm/min. The first measurable deflection from linearity will describe the proportional limit, the stress at which permanent or plastic deformation occurs; strength is defined as the stress at which a material fractures (44).

For diametral tensile testing, disk specimens, 5.1 mm in diameter and 1.6 mm in thickness, can be made, stored and tested as above (44).

Method of Use

In a further aspect of the present invention, it is provided a method of treating or ameliorating a disorder, comprising:

applying to a subject a composition comprising a powder component and a liquid component, and photo-setting the composition to cause it to reach an initial set immediately upon light curing after application to a subject and have a wet Vickers microhardness of about 0.1 GPa or higher;

wherein the powder component comprises calcium sulfate, wherein the liquid component comprises bisGMA (bisphenol-a-glycidyl methacrylate) and photoinitiators, and wherein the composition is a fast setting composition.

In some embodiments of the invention method, the powder component further comprises a silicate filler and a radioopacifier, and the liquid further optionally comprises HEMA (ydroxyethyl methacrylate), TEGDMA (triethylene glycol dimethacrylate), and/or polyacrylic acid and polyacrylic acid where each of HEMA, TEGMA, polyacrylic acid or combination thereof is optional.

In some embodiments of the invention method, optionally in combination with any or all of the above various embodiments, the liquid component further comprises water.

In some embodiments of the invention method, optionally in combination with any or all of the above various embodiments, the composition reaches an initial set immediately upon light curing after application to a subject, and having a wet Vickers microhardness of about 1 GPa or higher.

In some embodiments of the invention method, optionally in combination with any or all of the above various embodiments, the calcium sulfate comprises from 30-66% by weight of the composition.

In some embodiments of the invention method, optionally in combination with any or all of the above various embodiments, the bisGMA, photoinitiator, and silicate filler together comprise 10-30% by weight of the composition.

In some embodiments of the invention method, optionally in combination with any or all of the above various embodiments, the TEGDMA comprises 0-30% by weight of the composition.

In some embodiments of the invention method, optionally in combination with any or all of the above various embodiments, the polyacrylic acid comprises 0-40% by weight of the composition.

In some embodiments of the invention method, optionally in combination with any or all of the above various embodiments, the water comprises 6-15% by weight of the composition.

In some embodiments of the invention method, optionally in combination with any or all of the above various embodiments, the radio-opacifier comprises 4-10% by weight of the composition.

In some embodiments of the invention method, optionally in combination with any or all of the above various embodiments, HEMA comprises 0-15% by weight of the composition.

In some embodiments of the invention method, optionally in combination with any or all of the above various embodiments, the radio-opacifier is barium sulfate.

In some embodiments of the invention method, optionally in combination with any or all of the above various embodiments, the disorder is a pulpal disorder.

In some embodiments of the invention method, optionally in combination with any or all of the above various embodiments, the disorder is a bone defect or injury.

The subject can be an animal or a patient.

The composition of invention disclosed herein can be used to treat or ameliorating any dental or orthopedic conditions. An example of the dental condition is pulpal disorder.

As an example of use of the invention composition, these materials are mixed by hand, adding the powder and liquid components together and spatulating, placing in the desired place, and then command-set using a conventional dental curing light. We have tested the microhardness of these materials, many are harder than dentin, some are substantially harder than MTA. They have been tested in both wet and dry conditions, and have performed satisfactorily in both.

All of these components have been well studied and widely used in prior dental and medical products, materials and devices. This assures a smooth pathway through future biocompatibility testing and FDA approval.

In some embodiments, the composition of invention can be used in dental offices by dentists, general dentists, endodontists, pedodontists and others, as an alternative to existing materials for root end-filling during endodontic or root canal surgery; perforation repair of defects in the walls of tooth roots, pathological and iatrogenic; treating resorptive defects, where the wall of the tooth root has been eaten away by the body; treating vital exposed pulps due to deep decay; and obturating, or root canal filling, in immature non-vital teeth.

EXAMPLES

Example 1

Fabrication of CSRH Materials 5 exemplary CSRH materials were fabricated. When tested in a wet environment, as within wet dentin, adjacent to wet pulp, or wet periodontal ligament, or wet bone, all 5 CSRH materials were substantially harder than Grey MTA, White MTA or the fast setting calcium sulfate, gypsum after storage in 100% humidity for 10 days. The fast setting calcium gypsum or calcium sulfate was the major inorganic component of the CSRH materials. Clearly, the resin hybrid is superior to its parent calcium sulfate or gypsum, when tested in a wet environment. The Grey and White MTA materials displayed much higher hardness values when tested in a dry environment; however, they are called to serve in wet environments. This effect has been previously reported. The hardness values, reported here in GPA fall with the range previously reported for MTA (60-62). Interestingly, the standard deviations of the materials varied widely; a low standard deviation can provide greater clinical predictability—a critically important factor—and a tie-breaker. This data shows that these 5 initial CSRH materials indeed set well—a key prerequisite for clinical application. These 5 initial exemplary materials contained 0-12% HEMA; 20-40% polyacrylic acid; 25-50% bisGMA; 16-27% TEGDMA; and 15-30% water by weight in their liquid component. Feasibility of producing a family of CSRH materials, and one advantage has already been demonstrated.

TABLE 2

Vickers Microhardness of 5 Exemplary CSRH Materials and MTA controls

| Test Material | Test Environment | Vickers Microhardness (Std. Dev.) in GPa |
| --- | --- | --- |
| Grey MTA | Dry | 211 (44) |
| Grey MTA | Wet | 45 (9) |
| White MTA | Dry | 410 (133) |
| White MTA | Wet | 137 (49) |
| Fast setting gypsum | Dry | 226 (11) |
| Fast setting gypsum | Wet | 119 (7) |
| CSRH #1 | Wet | 528 (26) |
| CSRH #2 | Wet | 467 (102) |
| CSRH #3 | Wet | 551 (51) |
| CSRH #4 | Wet | 472 (43) |
| CSRH #5 | Wet | 306 (9) |

Example 2

Calcium Sulfate-resin Hybrid (CSRH) Endodontic Material

In this example, a new material—calcium sulfate-resin hybrid (CSRH)—for using in root canal surgery, repairing damaged roots and covering exposed pulps was developed. CSRH constituents, including calcium sulfate, or plaster, and dental resins, are known to be biocompatible. Unlike prior materials, SCRH both sets quickly and tolerates a wet surgical environment. We have made a variety of versions of this material with different proportions of their constituents. As an initial screening test, we measured the hardness of 10 different versions of this material. We found that 3 of the 10 versions had a hardness equivalent to or better than dentin which forms the bulk of a tooth root. The example and the test results in this example form the basis for further development of the CSRH material of invention for use in animals or people.

Materials and Methods:

A novel family of materials containing well-studied, biocompatible and widely used components was developed. Components included: calcium sulfate (30-60%); bisGMA photoinitiators and silicate fillers (10-30%); polyacrylic acid (0-10%); water (5-25%); HEMA (0-10%). 10 representative materials containing differing amounts of these constituents were made. Discoid specimens were made, 6 mm in diameter, 3 mm thick, stored in 100% humidity subjected to Vickers microhardness indentation (n=5), and descriptive statistics calculated.

Results:

The microhardness means and (standard deviations) of the 10 representative materials were: A 0.23 (0.01); B 0.23 (0.04); C 0.25 (0.05); D 0.28 (0.04); E 0.28 (0.07); F 0.29 (0.07); G 0.30 (0.10); H 0.38 (0.08); I 0.42 (0.10); and J 0.72 (0.03) GPa.

Discussion

Materials H-J were all either broadly equivalent to or harder than accepted values for human dentin. These materials will undergo further development then mechanical, physical, chemical, and biocompatibility testing in an iterative process to screen out those not suitable for clinical use, and facilitate optimization.

Conclusion:

A new family of endodontic materials—calcium sulfate resin hybrid (CSRH)—was developed; initial microhardness screening indicates that some of these materials can be suitable for eventual clinical use. Such CSRH materials can be used as an endodontic root-end filling, repair, obturating and pulp capping material. Such CSRH materials can have the advantages of both MTA and resin-modified glass-ionomers, the disadvantages of neither, but have superior physical properties, wider clinical application, and relatively low cost.

Example 3

Studies on Properties of CSRH Materials of Invention

Additional data on Vickers microhardness, tensile strength and compressive strength has been generated. This data confirms the feasibility of our approach to creating a usable calcium sulfate—resin hybrid (CSRH) fast-setting moisture-tolerant root canal retrofilling and repair material (Tables 3-5).

Vickers Microhardness Testing (Table 3)

Vickers microhardness testing was used to screen materials for adequacy of set. Initial set is critically important because surgical materials are exposed to moisture almost immediately and the surgical site must be quickly closed with full confidence that the repair material will set.

Specimens were formed in small discoid molds, height and diameter 3 mm; light cured as appropriate; stored in 100% humidity for 24 hours; embedded in epoxy resin; surface finished; and subjected to Vickers microhardness testing, each with 5 repetitions. Thirty different CSRH materials were tested as were 4 control materials: Grey MTA, the former market leader, closely related to Portland cement; White MTA, the current market leader, a variant based on Grey MTA; Geristore, a resin-composite glass-ionomer hybrid restorative material; and fast-setting dental plaster, a calcium sulfate material.

The data summarized in Table 3 show that most of the CSRH materials performed better than the Grey and White MTA controls; a couple performed better than Geristore; most performed better than calcium sulfate alone.

Compressive Strength (Table 4).

Although mechanical properties are not paramount for endodontic applications, because they are not load bearing and often replace pulpal soft tissue, ideally such materials should have reasonable properties so that they are unlikely to disintegrate.

Cylindrical specimens, 6 mm high and 4 mm in diameter, were made and stored at 37° C. in 100% humidity for 1 hour, before being transferred to water at 37° C. for an additional 23 hours. Wet specimens were loaded in compression at crosshead rates of 0.1 mm/min using a universal testing machine (Instron, Canton, Mass.), the failure load measured and compressive strength calculated, n=5 per material. Fifteen different CSRH materials were tested as were 3 control materials: White MTA, the current market leader, a variant based on Grey MTA; Geristore, a resin-composite glass-ionomer hybrid restorative material; and fast-setting dental plaster, a calcium sulfate material.

Unsurprisingly, Geristore, a resin-composite glass-ionomer, highly filled with fluoro alumina silica glass, had a very high compressive strength. Likewise, White MTA, a calcium silicate material related to Portland cement, had a good compressive strength. Three of the CSRH materials had compressive strengths greater than 5 MPa and were superior to the plain calcium sulfate.

Tensile Strength (Table 5)

Again, because these materials are not load bearing, mechanical properties are not paramount, but resistance to disintegration is important. In this regard, tensile strength may be more important than compressive strength because brittle materials are inherently weak in tension.

For diametral tensile testing, disk specimens, 5.1 mm in diameter and 1.6 mm in thickness, were made, stored and tested as above. Fifteen different CSRH materials were tested as were the same 3 control materials Unsurprisingly, Geristore, a resin-composite glass-ionomer, highly filled with fluoro alumina silica glass, had a very high tensile strength. White MTA, a calcium silicate material related to Portland cement, had a reasonable strength. One of the CSRH materials had a tensile strength higher than White MTA; 2 others closely followed. Four of the CSRH materials had tensile strengths superior to plain calcium sulfate. Importantly, the CSRH materials had lower standard deviations, or spread, than the White MTA giving confidence in a predictable outcome.

Other Testing.

Other studies on the CSRH material can include resistance to solubility and water absorption. Although a root canal retrofilling and repair material must have acceptable mechanical and physical properties, initial set, predictability, and ease of handling are paramount. Cost matters too, MTA is very expensive. Geristore demands an absolutely dry environment—difficult in a surgical field. MTA is difficult to handle and slow to set. All of the individual components of the CSRH materials are already separately used as components of dental surgical, endodontic, and restorative materials.

CONCLUSIONS

Many different examples of the CSRH materials had superior early hardness to the current market leader. Several examples of the CSRH materials had acceptable compressive strengths. Several examples of the CSRH materials had tensile strengths comparable to the current market leader.

TABLE 3

DIAMETRAL TENSILE STRENGTH in MPa (24 hours WET)

| Material Type | Test 1 | Test 2 | Test 3 | Test 4 | Test 5 | Mean (SD) | ADM resins (%) | BABS glass (%) | fumed silica (%) | sod HFS (%) | ethanol (%) | poly acrylic acid (%) | H2O (%) | CaSO4 (%) | HEMA (%) | barium sulfate (%) |
|---|---|---|---|---|---|---|---|---|---|---|---|---|---|---|---|---|
| Geristore | 22.4 | 18.4 | 24.7 | 22.5 | 19 | 21.4 (2.6) | NA | NA | NA | NA | NA | NA | NA | NA | NA | NA |
| CSRH 1 | 3.4 | 3.9 | 3.8 | 4 | 4 | 3.8 (0.2) | 10 | 1.5 | 1.5 | 0.1 | 4 | 8.6 | 8.6 | 57.1 | 0 | 8.6 |
| White MTA | 3.2 | 2.4 | 2 | 4 | 3.3 | 3.0 (0.8) | NA | NA | NA | NA | NA | NA | NA | NA | NA | NA |
| CSRH 24 | 2.7 | 2.4 | 2.8 | 2.7 | 2.8 | 2.7 (0.2) | 18.5 | 2.7 | 2.7 | 0.2 | 7.6 | 4.8 | 14.2 | 39.6 | 4.8 | 4.9 |
| CSRH 23 | 2.4 | 2.6 | 3.6 | 2.5 | 2.5 | 2.7 (0.5) | 13.5 | 2 | 2 | 0.2 | 5.4 | 0 | 18.5 | 39.8 | 13 | 5.6 |
| CSRH 17 | 2.4 | 2.6 | 2.4 | 2.5 | 2.5 | 2.5 (0.1) | 19 | 2.8 | 2.8 | 0.2 | 7.7 | 4.9 | 14.6 | 35 | 8.1 | 4.9 |
| CaSO4 | 2.6 | 2 | 2.4 | 2.2 | 2.9 | 2.4 (0.3) | NA | NA | NA | NA | NA | NA | NA | NA | NA | NA |
| CSRH 2 | 2.2 | 2.1 | 3 | 2.3 | 1.6 | 2.2 (0.5) | 13.5 | 2 | 2 | 0.2 | 5.3 | 13.8 | 10.3 | 46 | 0 | 6.9 |
| CSRH 18 | 2.1 | 2 | 2.5 | 1.6 | 2 | 2 (0.3) | 18.4 | 2.7 | 2.7 | 0.2 | 7.5 | 4.7 | 14.2 | 33.9 | 11 | 4.7 |
| CSRH 14 | 1.2 | 1.4 | 1.8 | 1.4 | 1.3 | 1.4 (0.4) | 19.7 | 2.9 | 2.9 | 0.3 | 7.8 | 10.1 | 0.1 | 36.1 | 5 | 5.1 |
| CSRH 11 | 1 | 0.9 | 1.1 | 1.4 | 1.5 | 1.2 (0.3) | 14 | 2 | 2 | 0.2 | 5.8 | 11.5 | 11.5 | 41.3 | 5.8 | 5.9 |
| CSRH 9 | 0.7 | 1.3 | 1 | 1.1 | 1.3 | 1.1 (0.2) | 15.2 | 2.2 | 2.2 | 0.2 | 6.2 | 16.7 | 9.4 | 41.7 | 0 | 6.2 |
| CSRH 7 | 0.5 | 0.3 | 0.5 | 0.9 | 0.9 | 0.6 (0.3) | 15.8 | 2.3 | 2.3 | 0.2 | 6.4 | 18 | 8.1 | 36 | 5.4 | 5.5 |
| CSRH 6 | 0.4 | 0.8 | 0.5 | 0.4 | 0.5 | 0.5 (0.2) | 16.7 | 2.4 | 2.4 | 0.2 | 6.9 | 19 | 8.6 | 38.1 | 0 | 5.7 |
| CSRH 10 | 0.3 | 0.7 | 0.4 | 0.6 | 0.6 | 0.5 (0.2) | 14.3 | 2.1 | 2.1 | 0.2 | 5.8 | 15.7 | 8.8 | 39.2 | 5.8 | 6 |
| CSRH 8 | 0.5 | 0.4 | 1.2 | 0.2 | 0.3 | 0.5 (0.4) | 16.3 | 2.4 | 2.4 | 0.2 | 6.5 | 18.5 | 8.3 | 37 | 2.8 | 5.6 |
| CSRH 28 | 0.1 | 0.6 | 0.1 | 0.7 | 1 | 0.5 (0.4) | 17.2 | 2.5 | 2.5 | 0.2 | 7 | 14.7 | 6.6 | 40.4 | 4.4 | 4.5 |
| CSRH 5 | 0.5 | 0.3 | 0.4 | 0.4 | 0.6 | 0.4 (0.1) | 16.4 | 2.4 | 2.4 | 0.2 | 6.6 | 15 | 8.4 | 37.4 | 5.6 | 5.6 |

TABLE 4

COMPRESSIVE STRENGTH in MPa (24 hours WET)

| Material Type | Test 1 | Test 2 | Test 3 | Test 4 | Test 5 | Mean (SD) | Opti. (%) | ADM resins (%) | BABS glass (%) | fumed silica (%) |
|---|---|---|---|---|---|---|---|---|---|---|
| Geristore | 101 | 74.3 | 87.5 | 96 | 83.3 | 88.4 (10.5) | NA | NA | NA | NA |
| White MTA | 15.1 | 17.1 | 10.2 | 14.3 | 19.5 | 15.2 (3.5) | NA | NA | NA | NA |
| CSRH 1 | 11.6 | 6 | 4.8 | 8.8 | 7.3 | 7.7 (2.6) | 17.1 | 10 | 1.5 | 1.5 |
| CSRH 23 | 6.1 | 6.4 | 5.7 | 7.5 | 6.3 | 6.4 (0.7) | 23.1 | 13.5 | 2 | 2 |
| CSRH 2 | 7.3 | 5.2 | 5.8 | 6 | 6.3 | 6.1 (0.8) | 23 | 13.5 | 2 | 2 |
| CaSO4 | 6.3 | 7.6 | 3.7 | 5.6 | 5.2 | 5.7 (1.4) | NA | NA | NA | NA |
| CSRH 11 | 4.6 | 4.8 | 5.4 | 4.2 | 4.4 | 4.7 (0.5) | 24 | 14 | 2 | 2 |
| CSRH 18 | 4.2 | 4.3 | 5.8 | 3.1 | 5.6 | 4.6 (1.1) | 31.5 | 18.4 | 2.7 | 2.7 |
| CSRH 24 | 6.5 | 7.2 | 2.5 | 1.6 | 3.2 | 4.2 (2.5) | 31.7 | 18.5 | 2.7 | 2.7 |
| CSRH 9 | 3.9 | 4.7 | 3.8 | 2.9 | 3.5 | 3.8 (0.7) | 26 | 15.2 | 2.2 | 2.2 |
| CSRH 17 | 1.9 | 2.1 | 4.7 | 2.2 | 3.3 | 2.8 (1.2) | 32.5 | 19 | 2.8 | 2.8 |
| CSRH 14 | 1.9 | 2.5 | 3.3 | 2.6 | 3.4 | 2.7 (0.6) | 33.6 | 19.7 | 2.9 | 2.9 |
| CSRH 28 | 1 | 1 | 2.1 | 1.9 | 2.5 | 1.7 (0.7) | 29.4 | 17.2 | 2.5 | 2.5 |
| CSRH 6 | 1.6 | 1.6 | 1.7 | 1.3 | 1.8 | 1.6 (0.2) | 28.6 | 16.7 | 2.4 | 2.4 |
| CSRH 10 | 1.7 | 1.5 | 1.5 | 1.2 | 1.9 | 1.6 (0.3) | 24.5 | 14.3 | 2.1 | 2.1 |
| CSRH 7 | 1.6 | 2 | 1.6 | 1.4 | 1.1 | 1.5 (0.3) | 27 | 15.8 | 2.3 | 2.3 |
| CSRH 5 | 1.7 | 1.4 | 1.2 | 0.9 | 0.7 | 1.2 (0.4) | 28 | 16.4 | 2.4 | 2.4 |
| CSRH 8 | 0.9 | 0.9 | 1.4 | 0.9 | 1.1 | 1.0 (0.2) | 27.8 | 16.3 | 2.4 | 2.4 |

COMPRESSIVE STRENGTH in MPa (24 hours WET)

| Material Type | sod HFS (%) | ethanol (%) | poly acrylic acid (%) | H2O (%) | CaSO4 (%) | HEMA (%) | barium sulfate (%) |
|---|---|---|---|---|---|---|---|
| Geristore | NA | NA | NA | NA | NA | NA | NA |
| White MTA | NA | NA | NA | NA | NA | NA | NA |
| CSRH 1 | 0.1 | 4 | 8.6 | 8.6 | 57.1 | 0 | 8.6 |
| CSRH 23 | 0.2 | 5.4 | 0 | 18.5 | 39.8 | 13 | 5.6 |
| CSRH 2 | 0.2 | 5.3 | 13.8 | 10.3 | 46 | 0 | 6.9 |
| CaSO4 | NA | NA | NA | NA | NA | NA | NA |
| CSRH 11 | 0.2 | 5.8 | 11.5 | 11.5 | 41.3 | 5.8 | 5.9 |
| CSRH 18 | 0.2 | 7.5 | 4.7 | 14.2 | 33.9 | 11 | 4.7 |
| CSRH 24 | 0.2 | 7.6 | 4.8 | 14.2 | 39.6 | 4.8 | 4.9 |
| CSRH 9 | 0.2 | 6.2 | 16.7 | 9.4 | 41.7 | 0 | 6.2 |
| CSRH 17 | 0.2 | 7.7 | 4.9 | 14.6 | 35 | 8.1 | 4.9 |
| CSRH 14 | 0.3 | 7.8 | 10.1 | 10.1 | 36.1 | 5 | 5.1 |
| CSRH 28 | 0.2 | 7 | 14.7 | 6.6 | 40.4 | 4.4 | 4.5 |
| CSRH 6 | 0.2 | 6.9 | 19 | 8.6 | 38.1 | 0 | 5.7 |
| CSRH 10 | 0.2 | 5.8 | 15.7 | 8.2 | 39.2 | 5.8 | 6 |
| CSRH 7 | 0.2 | 6.4 | 18 | 8.1 | 36 | 5.4 | 5.5 |
| CSRH 5 | 0.2 | 6.6 | 15 | 8.4 | 37.4 | 5.6 | 5.6 |
| CSRH 8 | 0.2 | 6.5 | 18.5 | 8.3 | 37 | 2.8 | 5.6 |

TABLE 5

VICKER'S MICROHARDNESS in GPa (24 hours in 100% humidity)

| Material Type | Test 1 | Test 2 | Test 3 | Test 4 | Test 5 | Mean (SD) | ADM resins (%) | BABS glass (%) | fumed silica (%) |
|---|---|---|---|---|---|---|---|---|---|
| CSRH 1 | 0.257 | 0.517 | 0.416 | 0.448 | 0.454 | 0.418 (0.097) | 10 | 1.5 | 1.5 |
| CSRH 2 | 0.325 | 0.371 | 0.418 | 0.491 | 0.306 | 0.382 (0.075) | 13.5 | 2 | 2 |
| Geristore | 0.351 | 0.374 | 0.347 | 0.29 | 0.28 | 0.323 (0.035) | NA | NA | NA |
| CSRH 5 | 0.331 | 0.233 | 0.38 | 0.404 | 0.161 | 0.302 (0.102) | 16.4 | 2.4 | 2.4 |
| CSRH 24 | 0.269 | 0.401 | 0.266 | 0.278 | 0.278 | 0.300 (0.058) | 18.5 | 2.7 | 2.7 |
| CSRH 9 | 0.29 | 0.288 | 0.287 | 0.283 | 0.29 | 0.288 (0.003) | 15.2 | 2.2 | 2.2 |
| CSRH 17 | 0.315 | 0.313 | 0.258 | 0.292 | 0.262 | 0.288 (0.027) | 19 | 2.8 | 2.8 |
| CSRH 7 | 0.357 | 0.19 | 0.251 | 0.327 | 0.312 | 0.287 (0.065) | 15.8 | 2.3 | 2.3 |
| CSRH 11 | 0.29 | 0.276 | 0.253 | 0.289 | 0.312 | 0.284 (0.022) | 14 | 2 | 2 |
| CSRH 28 | 0.242 | 0.295 | 0.303 | 0.268 | 0.28 | 0.278 (0.024) | 17.2 | 2.5 | 2.5 |
| CSRH 6 | 0.33 | 0.232 | 0.246 | 0.218 | 0.364 | 0.278 (0.065) | 16.7 | 2.4 | 2.4 |
| CSRH 10 | 0.257 | 0.287 | 0.26 | 0.346 | 0.237 | 0.277 (0.042) | 14.3 | 2.1 | 2.1 |
| CSRH 18 | 0.313 | 0.239 | 0.296 | 0.249 | 0.285 | 0.276 (0.031) | 18.4 | 2.7 | 2.7 |
| CSRH 14 | 0.265 | 0.297 | 0.244 | 0.242 | 0.274 | 0.264 (0.023) | 19.7 | 2.9 | 2.9 |
| CSRH 8 | 0.258 | 0.319 | 0.229 | 0.263 | 0.18 | 0.250 (0.051) | 16.3 | 2.4 | 2.4 |
| CSRH 23 | 0.252 | 0.251 | 0.219 | 0.238 | 0.22 | 0.236 (0.060) | 13.5 | 2 | 2 |
| CSRH 13 | 0.262 | 0.231 | 0.218 | 0.225 | 0.216 | 0.230 (0.019) | 18.4 | 2.7 | 2.7 |
| CSRH 4 | 0.248 | 0.187 | 0.232 | 0.252 | 0.281 | 0.230 (0.039) | 17 | 2.5 | 2.5 |
| CSRH 15 | 0.267 | 1.221 | 0.141 | 0.299 | 0.219 | 0.229 (0.060) | 14 | 2 | 2 |

TABLE 5-continued

| | | | | | | | | | |
|---|---|---|---|---|---|---|---|---|---|
| CSRH 3 | 0.234 | 0.232 | 0.232 | 0.204 | 0.222 | 0.225 (0.013) | 11.8 | 1.7 | 1.7 |
| CSRH 27 | 0.236 | 0.203 | 0.22 | 0.218 | 0.233 | 0.222 (0.013) | 17.8 | 2.6 | 2.6 |
| CSRH 19 | 0.219 | 0.222 | 0.205 | 0.248 | 0.21 | 0.221 (0.017) | 20.7 | 3 | 3 |
| CSRH 25 | 0.234 | 0.196 | 0.241 | 0.203 | 0.21 | 0.217 (0.020) | 17.8 | 2.6 | 2.6 |
| CSRH 20 | 0.195 | 0.174 | 0.222 | 0.245 | 0.202 | 0.208 (0.027) | 20.4 | 3 | 3 |
| CSRH 30 | 0.189 | 0.189 | 0.213 | 0.189 | 0.182 | 0.196 (0.012) | 16.8 | 2.4 | 2.4 |
| CSRH 21 | 0.179 | 0.174 | 0.192 | 0.196 | 0.188 | 0.186 (0.009) | 19 | 2.8 | 2.8 |
| CSRH 16 | 0.162 | 0.175 | 0.184 | 0.163 | 0.246 | 0.186 (0.035) | 19.7 | 2.9 | 2.9 |
| Grey MTA | 0.159 | 0.198 | 0.182 | 0.195 | 0.188 | 0.184 (0.016) | NA | NA | NA |
| CSRH 12 | 0.181 | 0.158 | 0.181 | 0.175 | 0.179 | 0.174 (0.010) | 16.1 | 2.3 | 2.3 |
| CSRH 26 | 0.191 | 0.178 | 0.196 | 0.156 | 0.146 | 0.173 (0.022) | 17.6 | 2.6 | 2.6 |
| CaSO4 | 0.174 | 1.174 | 0.16 | 0.161 | 0.161 | 0.166 (0.003) | NA | NA | NA |
| White MTA | 0.144 | 0.141 | 0.159 | 0.181 | 0.147 | 0.154 (0.016) | NA | NA | NA |
| CSRH 29 | 0.104 | 0.123 | 0.096 | 0.124 | 0.113 | 0.116 (0.009) | 17.6 | 2.6 | 2.6 |
| CSRH 22 | 0.086 | 0.084 | 0.108 | 0.101 | 0.087 | 0.107 (0.006) | 14.6 | 2.1 | 2.1 |

VICKER'S MICROHARDNESS in GPa (24 hours in 100% humidity)

| Material Type | sod HFS (%) | ethanol (%) | poly acrylic acid (%) | H20 (%) | CaS04 (%) | HEMA (%) | barium sulfate (%) |
|---|---|---|---|---|---|---|---|
| CSRH 1 | 0.1 | 4 | 8.6 | 8.6 | 57.1 | 0 | 8.6 |
| CSRH 2 | 0.2 | 5.3 | 13.8 | 10.3 | 46 | 0 | 6.9 |
| Geristore | NA | NA | NA | NA | NA | NA | NA |
| CSRH 5 | 0.2 | 6.6 | 15 | 8.4 | 37.4 | 5.6 | 5.6 |
| CSRH 24 | 0.2 | 7.6 | 4.8 | 14.2 | 39.6 | 4.8 | 4.9 |
| CSRH 9 | 0.2 | 6.2 | 16.7 | 9.4 | 41.7 | 0 | 6.2 |
| CSRH 17 | 0.2 | 7.7 | 4.9 | 14.6 | 35 | 8.1 | 4.9 |
| CSRH 7 | 0.2 | 6.4 | 18 | 8.1 | 36 | 5.4 | 5.5 |
| CSRH 11 | 0.2 | 5.8 | 11.5 | 11.5 | 41.3 | 5.8 | 5.9 |
| CSRH 28 | 0.2 | 7 | 14.7 | 6.6 | 40.4 | 4.4 | 4.5 |
| CSRH 6 | 0.2 | 6.9 | 19 | 8.6 | 38.1 | 0 | 5.7 |
| CSRH 10 | 0.2 | 5.8 | 15.7 | 8.8 | 39.2 | 5.8 | 6 |
| CSRH 18 | 0.2 | 7.5 | 4.7 | 14.2 | 33.9 | 11 | 4.7 |
| CSRH 14 | 0.3 | 7.8 | 10.1 | 10.1 | 36.1 | 5 | 5.1 |
| CSRH 8 | 0.2 | 6.5 | 18.5 | 8.3 | 37 | 2.8 | 5.6 |
| CSRH 23 | 0.2 | 5.4 | 0 | 18.5 | 39.8 | 13 | 5.6 |
| CSRH 13 | 0.2 | 7.5 | 10.8 | 10.8 | 36 | 5.4 | 5.5 |
| CSRH 4 | 0.2 | 6.9 | 17.4 | 8.7 | 38.8 | 0 | 6 |
| CSRH 15 | 0.2 | 5.8 | 5.8 | 17.3 | 41.3 | 5.8 | 5.8 |
| CSRH 3 | 0.2 | 4.8 | 12.1 | 12.1 | 43.4 | 6.1 | 6.1 |
| CSRH 27 | 0.2 | 7.3 | 4.6 | 13.7 | 42 | 4.4 | 4.8 |
| CSRH 19 | 0.3 | 8.4 | 5.3 | 15.9 | 38.1 | 0 | 5.3 |
| CSRH 25 | 0.2 | 7.3 | 15.3 | 6.9 | 38.2 | 4.6 | 4.5 |
| CSRH 20 | 0.3 | 8.1 | 0 | 17.4 | 37.4 | 5.2 | 5.2 |
| CSRH 30 | 0.2 | 7 | 4.3 | 12.9 | 39.6 | 10.1 | 4.3 |
| CSRH 21 | 0.2 | 7.7 | 0 | 16.3 | 35 | 11.4 | 4.8 |
| CSRH 16 | 0.3 | 7.8 | 5 | 15.1 | 36.1 | 5 | 5.2 |
| Grey MTA | NA | NA | NA | NA | NA | NA | NA |
| CSRH 12 | 0.2 | 6.6 | 11 | 11 | 39.4 | 5.5 | 5.6 |
| CSRH 26 | 0.2 | 7 | 4.5 | 13.4 | 37.3 | 10.4 | 4.4 |
| CaSO4 | NA | NA | NA | NA | NA | NA | NA |
| White MTA | NA | NA | NA | NA | NA | NA | NA |
| CSRH 29 | 0.2 | 7.1 | 15.4 | 6.9 | 42.3 | 0 | 5.3 |
| CSRH 22 | 0.2 | 6 | 0 | 20 | 43 | 6 | 6 |

REFERENCES CITED

1. Dorn S O, Gartner A H. Retrograde filling materials: a retrospective success-failure study of amalgam, EBA, and IRM. J Endod 1990; 16:391-3.
2. Shahi S. Rahimi M, Lofti et al. A comparative study of the biocompatibility of three root-end filling materials in rat connective tissue. J Endod 2006; 32:776 780.
3. Seung-Ho B, Lee W C, Setzer F C, Kim S. Periapical Bone Regeneration after Endodontic Microsurgery with Three Different Root-end Filling Materials: Amalgam, SuperEBA, and Mineral Trioxide Aggregate. J Endod 2010; 36:1323-1325.
4. Samara A, Sarri Y, Stravopodis D, Tzanetakis G N, Kontakiotis E G, Anastasiadou E. A Comparative Study of the Effects of Three Root-end Filling Materials on Proliferation and Adherence of Human Periodontal Ligament Fibroblasts. J Endod 2011; 37:865-870.
5. Cho E, Kopel H, White S N. Moisture susceptibility of resin-modified glass-ionomer materials. Quintessence international 1995; 26:351-8.
6. Huang G T. A paradigm shift in endodontic management of immature teeth: conservation of stem cells for regeneration. J Dent 2008; 36:379-86.
7. Witherspoon D E. Vital pulp therapy with new materials: new directions and treatment perspectives—permanent teeth. J Endod 2008; 34(7 Suppl):S25-S28.
8. Bogen G, Kim J S, Bakland L K. Direct pulp capping with mineral trioxide aggregate: an observational study. J An Dent Assoc 2008; 139:305-15.
9. Ng F K, Messer L B. Mineral trioxide aggregate as a pulpotomy medicament: an evidence-based assessment. Eur Arch Paed Dent 2008; 9:58-73.
10. Steffen R, Van Waes H. Understanding mineral trioxide aggregate/Portland-cement: a review of literature and background factors. Eur Arch Paed Dent 2009; 10:93-97.

11. Tang Y, Li X, Yin S. Outcomes of MTA as root-end filling in endodontic surgery: a systematic review. Quintessence Int 2010; 41:557-66.
12. Parirokh M, Torabinejad M. Mineral trioxide aggregate: a comprehensive literature review—Part I: chemical, physical, and antibacterial properties. J Endod 2010; 36:16-27.
13. Torabinejad M, Parirokh M. Mineral trioxide aggregate: a comprehensive literature review—Part II: leakage and biocompatibility investigations. J Endod 2010; 36:190-202
14. Parirokh M, Torabinejad M. Mineral trioxide aggregate: a comprehensive literature review—Part III: Clinical applications, drawbacks, and mechanism of action. J Endod 2010; 36:400-13.
15. Darvell B W, Wu R C. "MTA"-an Hydraulic Silicate Cement: review update and setting reaction. Dent Mater 2011; 27:407-22.
16. Bakland L K, Andreasen J O. Will mineral trioxide aggregate replace calcium hydroxide in treating pulpal and periodontal healing complications subsequent to dental trauma? A review. Dental Traumatol 2012; 28:25-32.
17. Torabinejad M, Hong C, Lee S J, Monsef M, Pitt Ford T R. Investigation of mineral trioxide aggregate for root-end filling in dogs. J Endod 1995; 21:603-608.
18. Torabinejad M, Chivian N. Clinical applications of mineral trioxide aggregate. J Endod 1999 25:197-205.
19. Jen D, Ko B, White S N, Glick D. In-vitro microleakage of amalgam, Super EBA, MTA and Geristore. J Endod 1998; 24:284, Abstract #OR52
20. Burstein J, Ko B, Glick D, White S N. 18 Month clinical trial of endodontic surgical retrofilling materials. J Endod 2001; 27:219 Abstract #OR 18
21. Gandolfi M G, Taddei P, Siboni F, Modena E, Ciapetti G, Prati C. Development of the foremost light-curable calcium-silicate MTA cement as root-end in oral surgery. Chemical-physical properties, bioactivity and biological behavior. Dental Materials 2011; 27:134-157.
22. Lee S J, Chung J, Na H S, Park E J, Jeon H J, Kim H C. Characteristics of novel root-end filling material using epoxy resin and Portland cement. Clin Oral Invest 2012: 1-7.
23. Thomas M V, Puleo D A, Al-Sabbagh M. Calcium sulfate: A review. J Long Term Eff Med Implants. 2005; 15:599-607.
24. Thomas M V, Puleo D A. Calcium sulfate: Properties and clinical applications. J Biomed Mater Res B Appl Biomater 2009; 88:597-610.
25. Payne J M, Cobb C M, Rapley J W, Killoy W J, Spencer P. Migration of human gingival fibroblasts over guided tissue regeneration barrier materials. J Periodontol 1996; 67:236-244.
26. Yamaguchi M, Yamaguchi T, Kaji H, Sugimoto T, Chihara K. Involvement of calcium-sensing receptor (CaR) in osteoblastic differentiation of mouse MC3T3-E1 cells. Am J Physiol Endocrinol Metab 2004; 3:E608-616.
27. Kameda T, Mano H, Yamada Y, Takai H, Amizuka N, Kobori M, Izumi N, Kawashima H, Ozawa H, Ikeda K, et al. Calcium-sensing receptor in mature osteoclasts, which are bone resorbing cells. Biochem Biophys Res Commun 1998; 245:419-422.
28. Walsh W R, Morberg P, Yu Y, Yang J L, Haggard W, Sheath P C, Svehla M, Bruce W J. Response of a calcium sulfate bone graft substitute in a confined cancellous defect. Clin Orthop 2003:228-236.
29. Scarano A, Artese L, Piattelli A, Carinci F, Mancino C, Iezzi G. Hemostasis control in endodontic surgery: a comparative study of calcium sulfate versus gauzes and versus ferric sulfate. J 2012; 38:20-3.
30. Pecora G, De Leonardis D, Ibrahim N, Bovi M, Cornelini R. The use of calcium sulphate in the surgical treatment of a 'through and through' periradicular lesion. Int Endod J. 2001; 34:189-97.
31. Mittal M, Chandra S, Chandra S. An evaluation of plaster of Paris barriers used under various materials to repair furcation perforations (in vitro study). J Endod. 1999; 25(5):385-8.
32. Taneja S, Kurnari M. Effect of internal matrices of hydroxyapatite and calcium sulfate on the sealing ability of mineral trioxide aggregate and light cured glass ionomer cement. J Consery Dent. 2011; 14:6-9.
33. Torabinejad M, Corr R, Handysides R, Shabahang S. Outcomes of Nonsurgical Retreatment and Endodontic Surgery: A Systematic Review. J Endod 2009; 35: 930-937.
34. Dragoo M R. Resin-ionomer and hybrid-ionomer cements: Part I. Comparison of three materials for the treatment of subgingival root lesions. The International journal of periodontics & restorative dentistry 1996; 16:594-601.
35. Dragoo M R. Resin-ionomer and hybrid-ionomer cements: part II, human clinical and histologic wound healing responses in specific periodontal lesions. The International journal of periodontics & restorative dentistry 1997; 17:75-87.
36. Fayazi S, Bayat S, White S N. Rapid management of type II dens invaginatus using an MTA plug: A case report. Accepted: Special Care Dentistry 2012
37. Tanaka K, Taira M, Shintani K, Wakasa K, Yamaki M. Residual monomers (TEGDMA and Bis-GMA) of a set visible-light-cured dental composite resin when immersed in water. J Oral Rehabil 1991; 18:353-362.
38. Sideridou I, Achilias D S, Spyroudi C, Karabela M. Water sorption characteristics of light-cured dental resins and composites based on Bis-EMA/PCDMA. Biomater 2004; 25:367-376.
39. Thorat S, Patra N, Ruffilli R, Diaspro A, Salerno M. Preparation and characterization of a BisGMA-resin dental restorative composites with glass, silica and titania fillers. Dent Mater J. 2012; 31:635-44.
40. Geurtsen W, Leyhausen G. Chemical-Biological Interactions of the resin monomer triethy-leneglycol-dimethacrylate (TEGDMA). J Dent Res 2001; 80:2046-2050.
41. Peutzfeldt A, Asmussen E. Effect of polyacrylic acid treatment of dentin on adhesion of glass ionomer cement. Acta Odontol Scand. 1990; 48:337-41.
42. Thijs H, Becer C R, Sanchez C, Fournier D, Hoogenbooma R and Schubert US. Water uptake of hydrophilic polymers determined by a thermal gravimetric analyzer with a controlled humidity chamber. Journal of Materials Chemistry 2007; 17:4864-4871.
43. Lioliou M G, Paraskeva C A, Koutsoukos P G, Payatakes A C. Calcium sulfate precipitation in the presence of water-soluble polymers. J Colloid Interface Sci 2006; 303:164-170.
44. White S N, Yu Z. Physical properties of fixed prosthodontic, resin composite luting agents. In J Prosthodont 1993; 6:384-389.
45. Li Z C, White S N. Mechanical properties of dental luting cements. J Prosthet Dent 1999; 81:597-609.
46. Spinner S, Tefft W E. A method for determining mechanical resonance frequencies and for calculating elastic moduli from these frequencies. American Society for Testing Materials Procedures 1961; 61:1121-38.

47. ASTM International. Standard test for dynamic Young's modulus, shear modulus, and Poisson's ratio for advanced ceramics by impulse excitation of vibration. ASTM Specification C1259. 1994.
48. British Standard Institution. Dental root canal sealing materials. BS EN ISO 6876. 2002.
49. Brännström M. Communication between the oral cavity and the dental pulp associated with restorative treatment. Oper Dent 1984; 9:57-68.
50. Torstenson B, Brännström M. Contraction gap under composite resin restorations: effect of hygroscopic expansion and thermal stress. Oper Dent 1988; 1:24-31.
51. Kakehasi S, Stanley H R, Fitzgerald R J. The effects of surgical exposures of dental pulps in germfree and conventional laboratory rats. J South Calif Dent Assoc. 1966; 34:449-51.
52. Madison S, Wilcox L R. An evaluation of coronal microleakage in endodontically treated teeth. Part III. In vivo study. J Endod. 1988; 14:455-8.
53. White S N, Sorensen J A, Kang S K, Caputo A A. Microleakage of new crown and fixed partial denture luting agents. J Prosthet Dent 1992; 67:156-161.
54. White S N, Yu Z, Tom J F, Sangsurasak S. In vivo microleakage of luting cements for cast crowns. The Journal of prosthetic dentistry 1994; 71:333-8.
55. White S N, Furuichi R, Kyomen S M. Microleakage through dentin after crown cementation. J Endod 1995; 21:9-12.
56. Rueggeberg F A, Hashinger D T, Fairhurst C W. Calibration of FTIR conversion analysis of contemporary dental resin composites. Dent Mater 1990; 6:241-9.
57. Hędzelek W, Marcinkowska A, Domka L, Wachowiak R. Infrared Spectroscopic Ident-ification of Chosen Dental Materials and Natural Teeth. Acta Physica Polonica A, 2008; 114: 471-84
58. Morales L G, Rocha R S, Menegazzo L M, de Araújo E B, Yukimito K. Infrared spectroscopy: a tool for determination of the degree of conversion in dental composites. Journal of Applied Oral Science 2008; 16:145-149.
59. Lee S Y, Greener E H, Menis D L. Detection of leached moieties from dental composites in fluids simulating food and saliva. Dental materials 1995; 11:348-353.
60. Namazikhah M S, Nekoofar M H, Sheykhrezae M S, Salariyeh S, Hayes S J, Bryant S T, Mohammadi M M, Dummer P M. The effect of pH on surface hardness and microstructure of mineral trioxide aggregate. Int Endod J 2008; 41:108-16.
61. Nekoofar M H, Oloomi K, Sheykhrezae M S, Tabor R, Stone D F, Dummer P M. An evaluation of the effect of blood and human serum on the surface microhardness and surface microstructure of mineral trioxide aggregate. Int Endod J 2010; 43:849-58.
62. Rhim E M, Huh S Y, Ahn S J, Abbott P V, Kim E C, Park S H. Comparison of the Microhardness and Morphology of Five Different Retrograde Filling Materials in Aqueous and Dry Conditions. Scanning 2012; 00:1-8.

Although the invention has been disclosed in the context of certain embodiments and examples, it can be understood by those skilled in the art that the embodiments of the invention extend beyond the specifically disclosed embodiments to other alternative embodiments and/or uses and modifications and equivalents thereof.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

We claim:

1. A polymerizable calcium sulfate-resin hybrid (CSRH) endodontic filling material composition, comprising a powder component and a liquid component,
   wherein:
   the powder component comprises calcium sulfate, a silicate filler, and a radio-opacifier
   the liquid component comprises bisGMA (bisphenol-a-glycidyl methacrylate) HEMA (hydroxyethyl methacrylate), TEGDMA (triethylene glycol dimethacrylate), polyacrylic acid and polymerization photoinitiators,
   the calcium sulfate powder component comprises from 30-66% by weight of the composition,
   the liquid component comprises 10-30% free water by weight of the composition,
   the bisGMA, photoinitiator, and silicate filler together comprise 6-15% by weight of the composition, and
   the composition achieves a wet Vickers microhardness of at least 0.1 GPA less than one minute after photo-initiation of polymerization of the composition.

2. The composition of claim 1, wherein the TEGDMA comprises up to 30% by weight of the composition.

3. The composition of claim 1, wherein the polyacrylic acid comprises up to 40% by weight of the composition.

4. The composition of claim 1, wherein the radio-opacifier comprises 4-10% by weight of the composition.

5. The composition of claim 1, wherein HEMA comprises up to 15% by weight of the composition.

6. The composition of claim 1, wherein the radio-opacifier is barium sulfate.

* * * * *